United States Patent [19]
Siebenhaar

[11] Patent Number: 5,977,290
[45] Date of Patent: Nov. 2, 1999

[54] BASIC CATALYSTS FOR THE ALDOL REACTION

[75] Inventor: Bernd Siebenhaar, Kandern, Germany

[73] Assignee: Novartis AG, Basel, Switzerland

[21] Appl. No.: 09/091,066

[22] PCT Filed: Dec. 2, 1996

[86] PCT No.: PCT/EP96/05327

§ 371 Date: Jun. 9, 1998

§ 102(e) Date: Jun. 9, 1998

[87] PCT Pub. No.: WO97/21659

PCT Pub. Date: Jun. 19, 1997

[30] Foreign Application Priority Data

Dec. 11, 1995 [CH] Switzerland .............................. 3493/95

[51] Int. Cl.$^6$ .............................. C08G 6/00; C08G 10/04
[52] U.S. Cl. .......................... 528/239; 528/220; 528/230; 502/64; 502/60; 502/78
[58] Field of Search ..................................... 528/239, 220, 528/230; 502/64, 60, 78

[56] References Cited

PUBLICATIONS

M. A. Aramendia et al., Chemistry Letters No. 4, 1995, pp. 279–280.
B. Danieli et al., HelveticaChimica Acta, vol. 76, No. 8, 1993, pp. 2981–2991.
A. Corma, et al., Journal of Catalysis 134, 58–62 (1992).
A. Corma, et al., Journal of Catalysis 130, 130–137 (1991).
Y. V. Subba Rao et al., Synthetic Communication, 21 (10 & 11), 1163–1166 (1991).

*Primary Examiner*—Duc Truong
*Attorney, Agent, or Firm*—Stephen G. Kalinchak; George R. Dohmann

[57] ABSTRACT

The invention relates to a process for the condensation of aldehydes or ketones with C—H acidic compounds (in particular Knoevenagel reaction) in the presence of at least one molecular sieve in the form of a zeolite or sheet silicate and one alkali carbonate, alkaline earth carbonate or ammonium carbonate as catalyst system. The products obtained are important intermediates or end products for the perfume industry.

16 Claims, No Drawings

BASIC CATALYSTS FOR THE ALDOL REACTION

The invention relates to a process for the condensation of aldehydes or ketones (carbonyl component) with C—H-acidic compounds (methylene component) in the presence of at least one molecular sieve in the form of a zeolite or sheet silicate and one alkali carbonate, alkaline earth carbonate or ammonium carbonate as catalyst system.

The Knoevenagel reaction is a special case of the aldol condensation where methylene components of particularly high C—H acidity are used. The reaction belongs to the standard methods of organic chemistry and is described, inter alia, in Principles of Organic Synthesis, R. O. C. Norman, Science Paperbacks 1970, pages 233–234. Basic catalysts are required for this reaction. Suitable catalysts are in particular nitrogen bases, especially organic bases such as piperidine, ammonium acetate, β-alanine in glacial acetic acid, or also alcoholates. This reaction procedure has the disadvantage of requiring the removal of the resulting water of reaction, which can be achieved e.g. by addition of toluene with azeotropic distillation. However, this requires temperatures of above 100° C. which is a big disadvantage in the case of temperature-sensitive compounds. During the processing of the product the base must be removed e.g. by distillation, which cannot always be achieved quantitatively and which can easily result in discoloured products.

The use of NaOH or $Na_2CO_3$ has also been known for a long time and is described, inter alia, by Bertini in Gazz. Chim. Ital. 31 I (1901), 266. One of its disadvantages is that it also requires removal of the water and that ester groups which may be present under these conditions can saponify again.

In recent times many attempts have been made to provide heterogeneous basic catalysts which can be easily removed after the reaction. The preparation of a catalyst by basic modification of hydrotalcite is described, inter alia, by A. Corma et al. in J. Catal. 134 (1992), 58–65. This preparation is extremely time-consuming. The resulting gel is dried repeatedly for 12 or 18 hours and calcinated. A Knoevenagel reaction at 130° C. is described using these catalysts. Another proposal, also by A. Corma et al. in J. Catal. 130 (1991), 130–137, is based on the partial exchange of the $Mg^{2+}$ ions in sepiolites, thereby increasing the basicity, and carrying out the reaction at lower temperatures. In this case, too, the catalyst needs to be prepared prior to use by a time-consuming ion exchange process.

B. M. Choudary et al. in Synthetic Comm., 21 (10 &11), 1163–1166 (1991) describe silylpropylethylenediamine-modified montmorillonites as solid basic catalysts for the Knoevenagel reaction. Although this catalyst can be easily removed and reused, its activity cannot fully satisfy. The preparation of this catalyst also requires a time-consuming reaction of 3-tri-ethoxysilylpropylethylenediamine with montmorillonite.

Surprisingly, it has now been found that it is possible to forego an elaborate catalyst preparation if the catalyst system used is a molecular sieve in the form of a zeolite or sheet silicate, additionally using alkali carbonate, alkaline earth carbonate or ammonium carbonate. This constitutes a catalyst system which is extremely easily accessible and which has excellent activity. Depending on the reactivity of the methylene component and on the melting point of both components, the aldol reactions can be carried out e.g. at room temperature. The reaction times are short, and the yield is high and often virtually quantitative.

It is not necessary to remove the water and no solvents need to be added for the azeotropic distillation. The product quality is excellent since no impurities can result from organic bases. The easy removal of the catalyst by filtration simplifies the working up of the product substantially.

The catalyst can be used again immediately after drying without any substantial loss in activity being observed even if this cycle is carried out repeatedly.

The invention relates to a process for the basically catalysed condensation of an aldehyde or ketone with a C—H-acidic compound, which comprises using as basic catalyst at least one alkali carbonate, alkaline earth carbonate or ammonium carbonate and at least one molecular sieve in the form of a zeolite, sheet silicate or a mixture thereof.

The aldehyde or ketone can contain unsubstituted or substituted aliphatic, cycloaliphatic, heteroaliphatic, heterocycloaliphatic, aromatic or heteroaromatic hydrocarbon radicals.

The aliphatic radical includes, for example, alkyl, in particular methyl, ethyl, i-propyl, n-propyl, n-butyl, i-butyl, t-butyl as well as the different isomeric pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl radicals.

The aliphatic radical also includes alkenyl, typically propenyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-octadec-2-enyl, n-octadec-4-enyl.

The substituted aliphatic radical can be hydroxyalkyl, typically hydroxymethyl, hydroxyethyl, 1-hydroxyisopropyl, 1-hydroxy-n-propyl, 2-hydroxy-n-butyl, 1-hydroxy-isobutyl, 1-hydroxy-secondary-butyl, 1-hydroxy-tertiary-butyl as well as the different isomeric pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl radicals.

The substituted aliphatic radical can also be haloalkyl, typically fluoromethyl, difluoromethyl, trifluoromethyl, chloromethyl, dichloromethyl, trichloromethyl, 2,2,2-trifluoroethyl, 2-fluoroethyl, 2-chloroethyl, 2,2,2-trichloroethyl as well as halogenated, preferably fluorinated or chlorinated alkanes, such as the isopropyl, n-propyl, n-butyl, isobutyl, sec-butyl, tert-butyl radical as well as the different isomeric pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl radicals.

Cyanoalkyl typically includes cyanomethyl (methyl nitrile), cyanoethyl (ethyl nitrile), 1-cyano-isopropyl, 1-cyano-n-propyl, 2-cyano-n-butyl, 1-cyano-isobutyl, 1-cyano-sec-butyl, 1-cyano-tert-butyl as well as the different isomeric cyanopentyl and cyanohexyl radicals.

Heteroaliphatic radical signifies that the aliphatic radical can be interrupted by one or more than one hetero a tom, typically O, S or N, and the above substituents can also occur. Where several hetero atoms are present, those radicals are preferred wherein the hetero atoms do not have any direct bond with one another.

Cycloalkyl is preferably $C_5$–$C_8$cycloalkyl, in particular $C_5$- or $C_6$cycloalkyl. Typical examples are cyclopropyl, dimethylcyclopropyl, cyclobutyl, cyclopentyl, methylcyclopentyl, cyclohexyl, cycloheptyl and cyclooctyl.

Heterocycloalkyl preferably contains 4 or 5 carbon atoms and one or two hetero atoms selected from the group consisting of O, S and N. Heterocycloalkyl can be, for example, oxirane, azirine, 1,2-oxathiolane, pyrazoline, pyrrolidine, piperidine, piperazine, morpholine, tetrahydrofuran or tetrahydrothiophene.

Aryl preferably contains 6 to 10 carbon atoms and can typically be phenyl, pentaline, indene, naphtalene, azuline or anthracene.

Heteroaryl preferably contains 4 or 5 carbon atoms and one or two hetero atoms selected from the group consisting of O, S and N. Heteroaryl can typically be pyrrole, furan, thiophene, oxazole, thiazole, pyridine, pyrazine, pyrimidine, pyridazine, indole, purine or quinoline.

Illustrative examples of substituents of the aliphatic, cycloaliphatic, heteroaliphatic, heterocycloaliphatic, aromatic or heteroaromatic hydrocarbon radicals or substituted hydrocarbon radicals are: halogen, —CN, —NO$_2$, R$_6$R$_7$R$_8$Si—(O)$_u$—, —COOM, —SO$_3$M, —PO$_3$M, —COO(M$_1$)$_{1/2}$, —SO$_3$(M$_1$)$_{1/2}$, —PO$_3$(M$_1$)$_{1/2}$, C$_1$–C$_{20}$alkyl, C$_1$–C$_{20}$hydroxyalkyl, C$_1$–C$_{20}$haloalkyl, C$_1$–C$_6$cyanoalkyl, C$_3$–C$_8$cycloalkyl, C$_6$–C$_{16}$aryl, C$_7$–C$_{16}$aralkyl, C$_3$–C$_6$heterocycloalkyl, C$_3$–C$_{16}$heteroaryl, C$_4$–C$_{16}$-heteroaralkyl or R$_{14}$—X$_1$—; or radicals, wherein two adjacent carbon atoms are unsubstituted or substituted by —CO—O—CO— or —CO—NR$_{10}$—CO—, or radicals, wherein an alicyclic, aromatic or heteroaromatic ring is fused to adjacent carbon atoms of the alicyclic ring; wherein X$_1$ is —O—, —S—, —CO—, —SO—, —SO$_2$—, —O—C(O)—, —C(O)—O—, —C(O)—NR$_{10}$—, —NR$_{15}$—C(O)—, —SO$_2$—O— or —O—SO$_2$—; R$_6$, R$_7$ and R$_8$ are each independently of one another C$_1$–C$_{12}$-alkyl, C$_1$–C$_{12}$perfluoroalkyl, phenyl or benzyl; R$_{14}$ is C$_1$–C$_{20}$alkyl, C$_1$–C$_{20}$haloalkyl, C$_1$–C$_{20}$-hydroxyalkyl, C$_3$–C$_8$cycloalkyl, C$_6$–C$_{16}$aryl, C$_7$–C$_{16}$aralkyl; R$_{10}$ and R$_{15}$ are each independently of the other hydrogen, C$_1$–C$_{12}$alkyl, phenyl or benzyl, the alkyl groups in turn being unsubstituted or substituted by C$_1$–C$_{12}$alkoxy or C$_3$–C$_8$cycloalkyl; M is an alkali and M$_1$ is an alkaline earth; and u is 0 or 1.

The carbonyl component is preferably a compound of formula I

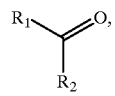

(I)

wherein

R$_1$ and R$_2$ are each independently of the other H, C$_1$–C$_{12}$alkyl, phenyl, phenyl-(C$_1$–C$_{12}$)alkyl, or phenyl or phenyl(C$_1$–C$_{12}$)alkyl, which is substituted by one or more than one halogen, C$_1$–C$_4$alkyl, C$_1$–C$_4$alkoxy, —OH or —COOR$_3$, and R$_3$ is H or C$_1$–C$_{12}$alkyl.

Halogen is fluoro, chloro, bromo or iodo.

The C$_1$–C$_{12}$alkyl radicals can be linear or branched, typically methyl, ethyl as well as the different positional isomers of propyl, butyl, pentyl, hexyl, heptyl, octyl, nonyl, decyl, undecyl or dodecyl.

Phenyl(C$_1$–C$_{12}$)alkyl is, for example, benzyl, phenethyl, 3-phenylpropyl, 4-phenylbutyl, 3-phenylbutyl, 2-phenylbutyl, 5-phenylpentyl, 4-phenylpentyl, 3-phenylpentyl, 2-phenylpentyl, or the different positional isomers of phenylhexyl, phenylheptyl, phenyloctyl, phenyinonyl, phenyldecyl, phenylundecyl or phenyidodecyl.

The C$_1$–C$_4$alkoxy radicals can be linear or branched and are, for example, methoxy, ethoxy as well as the different positional isomers of propoxy or butoxy.

C$_1$–C$_4$Alkyl-substituted phenyl typically includes methylphenyl, dimethylphenyl, trimethylphenyl, ethylphenyl, diethylphenyl, isopropylphenyl or tert-butylphenyl.

A preferred process is that wherein the carbonyl component is an aldehyde, so that R$_1$ is H.

R$_2$ is preferably phenyl, phenyl(C$_1$–C$_{12}$)alkyl, or phenyl or phenyl-(C$_1$–C$_{12}$)alkyl, which is substituted by one or more than one halogen, C$_1$–C$_4$alkyl, C$_1$–C$_4$alkoxy or —OH.

The aldehyde is particularly preferably a compound of formula Ia

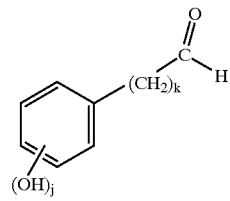

(Ia)

wherein j is 0 or 1, and k is 0 or a number from 1 to 6.

Suitable C—H-acidic compounds are, in addition to the compounds of of formula (I), in particular those which contain one or two electron-attracting adjacent to a methylene group.

The C—H-acidic compound is preferably a compound of formula II

(II)

wherein Z$_1$ and Z$_2$ are each independently of the other —COOR$_4$, —COOH, —CONHR$_4$, —COR$_4$, —CN, —SO$_2$R$_4$, —SR$_4$ or quarternary pyridine, and R$_4$ is C$_1$–C$_{12}$alkyl, or phenyl or naphthyl, which is unsubstituted or substituted by one or more than one halogen, CN, C$_1$–C$_{12}$alkyl or COO(C$_1$–C$_{12}$)alkyl.

Typical examples of alkali carbonates are Li$_2$CO$_3$, Na$_2$CO$_3$, K$_2$CO$_3$, Rb$_2$CO$_3$ or Cs$_2$CO$_3$, and typical examples of alkaline earth carbonates are MgCO$_3$, CaCO$_3$, SrCO$_3$ or BaCO$_3$. Carbonates of Na, K, Mg or Ca are preferred. It is also possible to use mixtures of different carbonates.

The alkali carbonates and alkaline earth carbonates are preferably used in an amount from 0.5 to 10.0 g, particularly preferably in an amount from 1.0 to 5.0 g, per mol of carbonyl component.

Molecular sieves in the form of zeolites are synthesised or naturally occuring crystalline hydrated aluminium silicates having a framework structure and containing exchangeable alkali cations or alkaline earth cations (definition according to D. W. Breck, Zeolite Molecular Sieves, J. Wiley, New York, 1974).

They can be characterised by the empirical formula M$_{2/n}$O•Al$_2$O$_3$•xSiO$_2$•yH$_2$O, wherein x≧2, y indicates the amount of bonded water molecules, and n is the valency of the alkali cation or alkaline earth cation M.

A survey of the properties and technical applications of these zeolites in the form of molecular sieves is offered, inter alia, by L. Puppe in Chemie in unserer Zeit 1986, pages 117 to 127.

For the application according to this invention it is possible to use naturally occuring as well as synthetically prepared molecular sieves in the form of zeolites. The molecular sieve zeolites are commercially available or, if they contain Rb or Cs ions, can be modified by ion exchange according to known methods.

Of the group of the molecular sieve zeolites the following are preferably used: zeolite A, zeolite ZSM-5, mordenite, zeolite L, zeolite X, zeolite Y, in their Na, K, or Ca form. If required, the Rb or Cs forms can be obtained by complete or partial ion exchange. It is also possible to use mixtures of different zeolites having different alkali ions. This opens up the possibility of adjusting the activity of the catalyst system to the reaction partners.

Preferred sheet silicates are those of the phyllosilicate class with Si atoms which are tetrahedrally surrounded by oxygen atoms. Two of these tetrahedral Si layers are linked by a layer of octahedrally coordinated metal such as Al or Mg via the oxygen atoms. This results in a layering consisting of tetrahedrons, octahedrons and tetrahedrons separated from the next repeating structural unit by a two-dimensional interspace. In this interspace, counterions may be present for the purpose of charge equalisation. Possible counterions are metal ions, oligometal ions, polyoxymetal ions or organic cations.

The use of phyllosilicates having a fibrous structure is particularly preferred. The hormite group in particular has the property of producing chainlike fibrous structures with channel-like voids; this group is particularly preferred.

A survey of the hormite group and its occurence may be found in Ullman Encyclopedia of Ind. Chem., 5th edition, 1986, VCH Verlag Weinheim, Vol A7, page 118.

Very particularly preferred fibrous sheet silicates are attapulgite or sepiolite.

Mixtures of different sheet silicates or zeolites with one another, or mixtures of sheet silicate with zeolite, are also very suitable.

The molecular sieves in the form of zeolites or sheet silicates preferably have voids of 1 to 15 Å, particularly preferably of 3 to 8 Å.

The molecular sieves are preferably used in the form of zeolites or sheet silicates in an amount from 5 to 50 g, particularly preferably from 10 to 20 g, per mol of carbonyl component.

The weight ratio of alkali carbonate, alkaline earth carbonate or ammonium carbonate to the molecular sieve in the form of zeolites and/or sheet silicates is preferably from 0.01:1 to 2:1.

The process is preferably carried out in the temperature range from 20° C. to 150° C., particularly preferably from 50 to 90° C.

The catalyst can be added in the form of the premixed components to the reaction mixture, but it is also possible to add the individual components in any order to the reaction mixture.

The reaction can be carried out with or without solvent. Preferably, no solvent is added if low-melting or liquid starting products are used. If solvents are used then e.g. toluene, xylene or an aliphatic hydrocarbon are very suitable.

The reaction is usually carried out without inert gas and under normal pressure conditions.

In another of its aspects, the invention relates to a catalyst mixture consisting of at least one alkali carbonate, alkaline earth carbonate or ammonium carbonate and at least one molecular sieve in the form of a zeolite, sheet silicate or a mixture thereof, as well as to the use of the catalyst mixture for the basic condensation of aldehydes and ketones having C—H-acidic compounds. The meanings and preferred meanings indicated above for the process also apply to the catalyst mixture and to the use thereof.

The products so obtained are important intermediates or end products for the perfume industry. In this connection DE-OS-2 256 483 cites a number of exemplary odiferous and aromatic substances.

The following Examples illustrate the invention.

EXAMPLE 1

10.61 g of benzaldehyde (0.1 mol) and 11.31 g of ethyl cyanoacetate (0.1 mol) are placed in a flask equipped with a reflux condenser and heated to 90° C. 1.0 g of zeolite A (supplied by Merck: MS 3 Å) and 0.5 g of $K_2CO_3$ are then added in succession. The reaction starts immediately and is complete after about 4 minutes. The reaction mixture is filtered while still hot, giving ethyl cyanocinnamate in a purity of >96%. The yield is 98%.

Working up variant

The hot reaction mixture is poured in 200 ml of ethanol, heated to 50–60° C. and then filtered. During cooling, the ethyl cyanocinnamate crystallises out in a purity of 99%. The yield is 96%.

The following reactions are carried out in general accordance with the procedure of Example 1, using in each case 0.45 g of $K_2CO_3$ and 2 g of zeolite A (supplied by Merck: MS 3 Å) as well as 0.1 mol of benzaldehyde and 0.1 mol of C—H-acidic compound.

| C—H-acidic cmpd | Temp. [°C.] | Time [h] | Sel. product [%] | Yield product [%] | Product |
|---|---|---|---|---|---|
| malonodinitrile | 70 | 0.25 | 99.9 | 97.8 | benzylidene malonodinitrile |
| ethyl acetate | 90 | 0.50 | 100.0 | 64.2 | ethyl acetocinnamate |
| ethyl acetate | 90 | 4.00 | 98.8 | 54.1 | ethyl acetocinnamate |
| ethyl acetate | 120 | 0.50 | 95.3 | 54.8 | ethyl acetocinnamate |
| diethyl malonate | 150 | 1.50 | 86.6 | 53.9 | diethyl benzylidenemalonate |
| diethyl malonate | 130 | 1.50 | 87.8 | 57.6 | diethyl benzylidenemalonate |

The following reactions are carried out in general accordance with the procedure of Example 1, using in each case 0.45 g of $K_2CO_3$ and 2 g of zeolite A (supplied by Merck: MS 4 Å) as well as 0.1 mol of carbonyl component and 0.1 mol of ethyl cyanoacetate.

| Carbonyl component | Temp. [°C.] | Time [h] | Sel. product [%] | Yield [%] | Product |
|---|---|---|---|---|---|
| vanillin | 30 | 3.00 | 95.70 | 61.05 | ethyl 3-methoxy-4-hydroxy-2-cyanocinnamate |
| octanal | 50 | 0.25 | 98.55 | 77.28 | ethyl 2-cyano-2-decenate |
| octanal | 50 | 0.50 | 98.77 | 78.68 | ethyl 2-cyano-2-decenate |
| octanal | 50 | 2.00 | 90.82 | 80.00 | ethyl 2-cyano-2-decenate |
| benzalacetone | 90 | 5.00 | 98.30 | 81.33 | ethyl 2-cyano-3-methyl-5-phenyl-pentenate |

EXAMPLE 2

(recycling)

The catalyst mixture according to Example 1 is filtered and the filtration product is washed with toluene and dried under vacuum at 120° C. for 5 hours. The reaction described in Example 1 is then carried out using this recycled catalyst. There is no noticable loss in reactivity.

The procedure is repeated 4 times in all without the catalyst showing any loss in reactivity.

EXAMPLE 3

0.1 mol each of benzaldehyde (10.61 g) and acetophenone (12.01 g) are placed in a flask equipped with a reflux condenser and then 0.7 g of $K_2CO_3$ and 2 g of zeolite A (supplied by Merck: MS 4 Å) are added at room temperature (about 22° C.). The mixture is then heated to 50° C. and stirred for 3 h. The catalyst mixture is filtered and the reaction mixture is taken up in 200 ml of methanol while still hot. The benzalacetophenone product (chalcone) is obtained in a purity of >96%. The yield is 55%.

What is claimed is:

1. A process for the basically catalysed condensation of an aldehyde or ketone with a C—H acidic compound, which process comprises reacting the aldehyde or ketone with the acidic C—H compound wherein the basic catalyst comprises at least one alkali carbonate, alkaline earth carbonate or ammonium carbonate and at least one molecular sieve in the form of a zeolite, sheet silicate or a mixture thereof.

2. A process according to claim 1, wherein the aldehyde or ketone is a compound of formula I

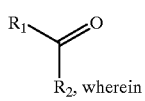

$R_1$ and $R_2$ are each independently of the other H, $C_1$–$C_{12}$alkyl, phenyl, phenyl-($C_1$–$C_{12}$)alkyl, or phenyl or phenyl($C_1$–$C_{12}$)alkyl which is substituted by one or more than one halogen, $C_1$–$C_4$alkyl, $C_1$–$C_4$alkoxy, —OH or —$COOR_3$, and $R_3$ is H or $C_1$–$C_{12}$alkyl.

3. A process according to claim 1, wherein an aldehyde is reacted.

4. A process according to claim 2, wherein $R_1$ is H, and $R_2$ is phenyl, phenyl($C_1$–$C_{12}$)alkyl, or phenyl or phenyl ($C_1$–$C_{12}$)alkyl which is substituted by one or more than one halogen, $C_1$–$C_4$alkyl, $C_1$–$C_4$alkoxy or —OH.

5. A process according to claim 1, wherein the C—H-acidic compound is a compound of formula II

wherein $Z_1$ and $Z_2$ are each independently of the other —$COOR_4$, —COOH, —$CONHR_4$, —$COR_4$, —CN, —$SO_2R_4$, —$SR_4$ or quaternary pyridine, and $R_4$ is $C_1$–$C_{12}$alkyl, or phenyl or naphthyl which is unsubstituted or substituted by one or more than one halogen, CN, $C_1$–$C_{12}$alkyl or $COO(C_1$–$C_{12})$alkyl.

6. A process according to claim 1, wherein the carbonate is selected from the group consisting of $Li_2CO_3$, $Na_2CO_3$, $K_2CO_3$, $Rb_2CO_3$, $Cs_2CO_3$, $MgCO_3$, $CaCO_3$, $SrCO_3$, $BaCO_3$ and $(NH_4)_2CO_3$.

7. A process according to claim 1, which comprises using the alkali carbonate, alkaline earth carbonate or ammonium carbonate in an amount from 0.5 to 10.0 g per mol of carbonyl component.

8. A process according to claim 1, which comprises using as molecular sieve zeolite A, zeolite ZSM-5, mordenite, zeolite L, zeolite X or zeolite Y in their Ca, Na, K, Rb or Cs form, or a mixture thereof.

9. A process according to claim 1, wherein the sheet silicate is phyllosilicate.

10. A process according to claim 1, which comprises using the molecular sieves in the form of zeolites or sheet silicates in an amount from 5 to 50 g per mol of carbonyl component.

11. A process according to claim 1, wherein the weight ratio of alkali carbonate, alkaline earth carbonate or ammonium carbonate to the molecular sieve in the form of a zeolite and/or sheet silicate is from 0.01:1 to 2:1.

12. A process according to claim 1, which is carried out in the temperature range from 20° C. to 150° C.

13. A process according to claim 1, which comprises removing the catalyst after the condensation reaction, drying it and reusing it.

14. A catalyst mixture consisting of at least one alkali carbonate, alkaline earth carbonate or ammonium carbonate and at least one molecular sieve in the form of a zeolite, sheet silicate or a mixture thereof.

15. A process according to claim 2, wherein the C—H acidic compound is also a compound of formula I.

16. A process according to claim 1, wherein the carbonate and molecular sieve are added separately to the reaction.

* * * * *